(12) United States Patent
Ditzel et al.

(10) Patent No.: US 8,158,815 B2
(45) Date of Patent: Apr. 17, 2012

(54) CARBONYLATION PROCESS WITH IN SITU REGENERATION OF MORDENITE CATALYST

(75) Inventors: Evert Jan Ditzel, Goole (GB); David John Law, Beverley (GB); George Ernest Morris, Cottingham (GB); Mark Stephen Roberts, Beverley (GB); Stephan Andreas Schunk, Heidelberg (DE); Martin Smit, Bloemendaal (NL); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 65 days.

(21) Appl. No.: 12/735,123

(22) PCT Filed: Dec. 16, 2008

(86) PCT No.: PCT/GB2008/004144
§ 371 (c)(1),
(2), (4) Date: Aug. 9, 2010

(87) PCT Pub. No.: WO2009/077745
PCT Pub. Date: Jun. 25, 2009

(65) Prior Publication Data
US 2010/0317888 A1    Dec. 16, 2010

(30) Foreign Application Priority Data
Dec. 19, 2007 (EP) .................................. 07254958

(51) Int. Cl.
*C07C 67/36* (2006.01)
*C07C 51/12* (2006.01)
*C07C 53/08* (2006.01)

(52) U.S. Cl. .................. 560/232; 562/519; 562/607

(58) Field of Classification Search .................. None
See application file for complete search history.

(56) References Cited

U.S. PATENT DOCUMENTS
5,196,621 A    3/1993    Diesen et al.

FOREIGN PATENT DOCUMENTS
WO    WO 2007/128955    11/2007

OTHER PUBLICATIONS

International Search Report for PCT/GB2008/00004144, mailed May 13, 2009.
Written Opinion of the International Searching Authority for PCT/GB2008/00004144, mailed May 13, 2009.
Ellis, B. et al., "Heterogeneous catalysts for the direct, halide-free carbonylation of methanol" 11th International Congress on Catalysis—40th Anniversary. ICC '96, vol. 101, No. Part B, (Jun. 30, 1996), pp. 771-779.

*Primary Examiner* — Paul A Zucker
(74) *Attorney, Agent, or Firm* — Nixon & Vanderhye (57) ABSTRACT

A process for the carbonylation of dimethyl ether, dimethyl carbonate and/or methanol with carbon monoxide and hydrogen in the presence of a mordenite catalyst to produce at least one of acetic acid and methyl acetate in which process the mordenite catalyst is regenerated in-situ by contacting the catalyst with a regenerating gas comprising a molecular oxygen-containing gas and an inert diluent at a total pressure in the range 1 to 100 bar and wherein the partial pressure of the molecular oxygen-containing gas is such that the temperature of the catalyst is maintained within the range 225 to 325° C.

15 Claims, 10 Drawing Sheets

CARBONYLATION PROCESS WITH IN SITU REGENERATION OF MORDENITE CATALYST

This application is the U.S. national phase of International Application No. PCT/GB2008/004144 filed 16 Dec. 2008, which designated the U.S. and claims priority to EP Application No. 07254958.7 filed 19 Dec. 2007, the entire contents of each of which are hereby incorporated by reference.

This invention relates to a carbonylation process in which a zeolite catalyst is regenerated in-situ, and, in particular to the in-situ regeneration of mordenite in the carbonylation of methanol, dimethyl ether and/or dimethyl carbonate.

Zeolites, such as mordenite and ferrierite are known to be suitable for use as catalysts for the carbonylation of feedstocks such as methanol, dimethyl ether and dimethyl carbonate to produce the carbonylation products methyl acetate and/or acetic acid.

EP-A-0 596 632 describes a vapour phase process for the carbonylation of methanol to produce acetic acid in the presence of a modified mordenite catalyst at high temperatures and pressures.

WO 2005/105720 describes a process for production of a carboxylic acid and/or an ester or anhydride thereof by carbonylating an aliphatic alcohol or reactive derivative thereof with carbon monoxide in the substantial absence of halogens in the presence of a modified mordenite catalyst at a temperature in the range 250 to 600° C. and at a pressure in the range 10 to 200 bar.

WO 2006/121778 describes a process for the production of a lower alkyl ester of a lower aliphatic carboxylic acid by carbonylating under substantially anhydrous conditions a lower alkyl ether with carbon monoxide in the presence of a mordenite or ferrierite catalyst.

U.S. Pat. No. 4,612,387 describes a method for making monocarboxylic acids and esters comprising contacting carbon monoxide and a monohydric alcohol containing 1 to 4 carbon atoms in the presence of a crystalline aluminosilicate zeolite having a silica to alumina ratio at least about 6 and a constraint index within the approximate range of 1 to 12 under a pressure of at least one atmosphere.

'Heterogeneous catalysts for the direct, halide-free carbonylation of methanol' by Ellis et al, Studies in Surface Science and Catalysis, Vol. 111, pages 771-779, 1996, describes the catalyst preparation, performance and physical characterisation of Cu-mordenite compared to H-mordenite.

However, although mordenite is a highly effective carbonylation catalyst, it has been found that it undergoes deactivation with time during the carbonylation reaction. Without wishing to be bound by theory, it is believed that loss in activity and/or selectivity is at least partly due to the formation of hydro carbonaceous deposits (coke) which prevent access to the catalytically active sites of the zeolite. Thus, there remains a need for a method for treating a deactivated mordenite zeolite catalyst, in-situ, in order to at least partially restore activity whilst maintaining selectivity to acetyls products.

It has now been found that catalyst activity may be at least partially restored whilst maintaining selectivity to the desired acetyls products by treating a deactivated mordenite zeolite catalyst with a molecular oxygen-containing gas at low temperatures.

Accordingly, the present invention provides a process for the production of at least one of methyl acetate and acetic acid by the carbonylation in a reactor of a carbonylatable reactant selected from methanol, dimethyl ether and dimethyl carbonate with carbon monoxide in the presence of a mordenite zeolite catalyst in which process the catalyst is regenerated in-situ by contacting the catalyst with a regenerating gas comprising a molecular oxygen-containing gas and an inert diluent at a total pressure in the range 1 to 100 bar and wherein the partial pressure of the molecular oxygen-containing gas is such that the temperature of the catalyst is maintained in the range 225 to 325° C.

The zeolite to be regenerated in the carbonylation process of the present invention is mordenite. Mordenite is known to catalyse the carbonylation of methanol, dimethyl ether or dimethyl carbonate with carbon monoxide to produce at least one of methyl acetate and acetic acid. The structural and topological details of mordenite are well-known and are detailed in, for example, the *Atlas of Zeolite Framework Types* (C. Baerlocher, W. M. Meier, D. H. Olson, $5^{th}$ ed. Elsevier, Amsterdam, 2001) and its web-based version at (http://www.iza-structure.org/databases/). These compendia provide structural information on all zeolite framework types which have been approved by the Structure Commission of the International Zeolite Association. Mordenite in the hydrogen form has elliptical 6.5×7.0 Angstrom channels (12 member rings with window openings running in the crystallographical c-direction). It also has a system of smaller channels running perpendicular to the 12 member ring channels (and running in the b-direction). These small channels consist of 3.4×4.8 Angstrom channels having 8 member ring windows of these dimensions. The mordenite structure also possesses a zig-zag Y-branching of the pore structure due to twisted 8 member rings (in the crystallographic c-direction) this results in a distorted window to each side of the Y-branching of 2.6×5.7 Angstroms.

Preferably, the mordenite for use in the present invention has a silica:$X_2O_3$ molar ratio of at least 5, for example, 5 to 90:1, wherein X is selected from aluminium, boron, iron, gallium and mixtures thereof. Generally, X will be aluminium except where framework aluminium atoms have been replaced by one or more of boron, iron and gallium. Typically, the mordenite zeolite will have a silica:alumina molar ratio in the range 6 to 90:1, such as 10 to 40:1.

Mordenite is available from commercial sources, generally in the Na, $NH_4$ form or H-form of the mordenite. The $NH_4$ form of mordenite can be converted to the acid form (H-form) by known techniques, such as calcination at high temperature. The Na form of mordenite can be converted to the acid form (H-form) by converting first to an $NH_4$ form by ion exchange with ammonium salts such as ammonium nitrate. Alternatively, mordenite may be synthesised using known techniques.

For use as the catalyst in a carbonylation process to produce methyl acetate and/or acetic acid, the mordenite may be employed in the acid form (H-form) or it may be optionally ion-exchanged or otherwise loaded with one or more metals such as copper, silver, gold, nickel, iridium, rhodium, platinum, palladium or cobalt, preferably, at least one of copper and silver.

The metal loading on the mordenite may be expressed in terms of the fractional loading of the metal as gram atoms of metal per gram atom of aluminium in the mordenite. The metal loading can also be expressed as a mole percentage loading relative to aluminium in the mordenite through the relationship:

mol % Metal=(gram atoms Metal/gram atoms aluminium)×100

Thus, for example, a loading of 0.55 gram atoms of copper per aluminium in the mordenite equates to a 55 mol % loading of copper relative to aluminium in the mordenite.

Suitably, the metal loading may be in the range of 1 to 200 mol % relative to aluminium, for example, 5 to 120 mol %, such as 5 to 110 mol %.

In the process of the present invention, the mordenite catalyst is contacted with a regenerating gas comprising a molecular oxygen-containing gas and an inert diluent.

The molecular oxygen-containing gas may be molecular oxygen, air or a gas richer or poorer in molecular oxygen than air.

The molecular oxygen-containing gas is used in diluted form by diluting with any suitable inert diluent, for example nitrogen, helium, argon, carbon dioxide or a mixture thereof, such as a mixture of nitrogen and helium or a mixture of nitrogen and carbon dioxide.

Suitably, the regenerating gas may comprise oxygen and an inert diluent selected from nitrogen, carbon dioxide and mixtures thereof. Alternatively, the regenerating gas may comprise air and an inert diluent selected from nitrogen, carbon dioxide and mixtures thereof.

The catalyst is contacted with a pre-mixed feed of the molecular oxygen-containing gas and the inert diluent.

The concentration of the molecular oxygen-containing gas is preferably kept low to prevent reaction exotherms and/or damage to the catalyst. Suitably, the concentration of the molecular oxygen-containing gas, such as oxygen or air, in the regenerating gas may be in the range 0.1 mol % to 25 mol %, such as 0.5 to 20 mol % based on the total of the concentration of the molecular oxygen-containing gas and the concentration of the inert diluent. During the regeneration, the concentration of the molecular oxygen-containing gas in the regenerating gas may be increased to enhance the removal of coke.

The partial pressure of the molecular oxygen-containing gas, such as air or oxygen, is such that the temperature of the catalyst is maintained in the range 225 to 325° C. to at least substantially maintain the selectivity to acetyls product compared to the selectivity achieved immediately prior to regeneration. The temperature of a catalyst bed can be determined using known techniques, for example, by using thermocouples. Thermocouples can be placed along a catalyst bed to determine the temperature profile of the catalyst bed. The amount of molecular oxygen-containing gas entering the reactor can then be controlled so as to maintain the catalyst bed in the temperature range of 225 to 325° C.

Suitably, at a total pressure in the range 1 to 100 bar, the partial pressure of the molecular oxygen-containing gas may be, for example, less than 1.5 bar and preferably less than 1.0 bar, for example, 0.05 to 2, such as in the range 0.05 bar to 1.5 bar or 0.18 to 1.4 bar.

The regeneration is carried out at a catalyst temperature in the range 225 to 325° C., preferably in the range 250 to 300° C.

The regeneration is carried out at a total pressure in the range 1 to 100 bar, such as 1 to 80 bar.

Suitably, the regeneration is carried out at a catalyst temperature in the range 250 to 300° C. and at a total pressure in the range 1 to 80 bar.

During the regeneration, the partial pressure of the molecular oxygen-containing gas may be adjusted. Additionally or alternatively, the temperature may be adjusted. For example, during the course of a single generation, the partial pressure of the molecular oxygen-containing gas may be increased, the temperature of the catalyst may be increased or both the catalyst temperature and partial pressure of the molecular oxygen-containing gas may be increased. Where the partial pressure of the molecular oxygen-containing gas is adjusted and/or the temperature is adjusted during a regeneration, the adjustment should not be such that the temperature of the catalyst falls outside the temperature range of 225 to 325° C.

The gas hourly space velocity (GHSV) of the regeneration gas may suitably be in the range 500 to 10,000 $h^{-1}$.

The period over which the catalyst is contacted with the regenerating gas is chosen such that activity of the catalyst is greater than the activity immediately prior to the start of the regeneration process. Typically, the contact period is in the order of hours, such as in the range 1 to 100 hours.

The regeneration of the catalyst is conducted 'in-situ'. By 'in-situ' is meant that a carbonylation reaction is ceased, the regeneration process is carried out and then the carbonylation reaction is restarted. In this manner, it is not necessary to remove the catalyst from the carbonylation reactor.

To carry out the regeneration in-situ, the carbonylatable reactant, carbon monoxide, and where used, hydrogen, feeds to the reactor are ceased. In addition, to prevent potential safety hazards, prior to introducing the molecular oxygen-containing gas used for the regeneration, the reactor may be purged with an inert gas, such as nitrogen and/or helium to remove volatile components such as carbon monoxide, hydrogen, methyl acetate, light hydrocarbons and dimethyl ether contained therein. Where the carbonylation reaction is carried out at temperature which is different to that used for the regenerating procedure, the temperature of the catalyst bed is adjusted to the required temperature by any suitable means such as by heat exchange. The temperature is adjusted so that the temperature of the catalyst is in the range 225 to 325° C. Once the catalyst bed is at the required temperature, the regenerating gas comprising the molecular oxygen containing gas and an inert diluent is introduced into the reactor and contacted with the catalyst for a period of time to effect regeneration of the catalyst to restore catalytic activity and/or selectivity by removing hydrocarbon deposits from the catalyst after which time the regeneration is terminated. After terminating the regeneration process, the reactor may be purged with an inert gas to remove molecular oxygen-containing gas remaining in the reactor. Contact of the catalyst with the carbonylatable reactant, carbon monoxide and, optionally, hydrogen may then be resumed.

Catalyst regeneration may be performed once over the course of a carbonylation process or it may be repeated one or more times, such as four times, without significantly affecting the catalyst's performance. The catalyst may be regenerated in a first regeneration and then subjected to at least one subsequent, such as at least two subsequent regenerations, for example, up to four subsequent regenerations, during the course of the carbonylation process. Suitably, catalyst regeneration may be carried out 1 to 5 times over the course of a carbonylation process. Each regeneration may be carried out under the same or different regeneration conditions. Suitably, where the regeneration is repeated, the first regeneration may be carried out under a different catalyst temperature and/or partial pressure of the molecular oxygen-containing gas to that employed in a subsequent regeneration. For example, a first regeneration may be carried out at a lower temperature than a subsequent regeneration or a subsequent regeneration may be carried out at a higher molecular oxygen-containing gas partial pressure than the first regeneration.

Alternatively, the first regeneration may be carried out at the same catalyst temperature and/or partial pressure of the molecular oxygen-containing gas to that employed in a subsequent regeneration. For example, a subsequent regeneration may be carried out at a higher catalyst temperature than that employed in the first or a previous regeneration. A subsequent regeneration may also be carried out using a higher partial pressure of molecular oxygen-containing gas than that employed in the first or a previous regeneration.

The regeneration is carried out in-situ in the production of at least one of methyl acetate and acetic acid by the carbonylation of a carbonylatable reactant selected from dimethyl ether, dimethyl carbonate and methanol.

Where dimethyl ether or dimethyl carbonate is used as the carbonylatable reactant, the carbonylation process is carried out by passing the dimethyl ether or dimethyl carbonate, carbon monoxide and, where used, hydrogen through, for example, a fixed or fluidised bed of mordenite catalyst maintained at the required temperature, such as in the range 150 to 350° C., such as 250 to 350° C. The process is typically carried out under substantially anhydrous conditions, that is less than 2.5 wt % water in the dimethyl ether or dimethyl carbonate feed and at a total reaction pressure in the range 1 to 100 bar and a gas hourly space velocity in the range 500 to 40,000 $h^{-1}$.

Suitably, in the carbonylation of dimethyl ether using H-mordenite or a metal loaded mordenite such as a copper or silver loaded mordenite catalyst at a total pressure of 70 bar, regeneration of the catalyst may be carried out in a single regeneration using oxygen and nitrogen and wherein the oxygen partial pressure is initially 0.7 bar and is then raised to 1.4 bar. Catalyst regeneration may be repeated, for example 1 to 5 times.

Where methanol is used as the carbonylatable reactant, the carbonylation process is carried out by passing methanol, carbon monoxide and, where used, hydrogen through, for example, a fixed or fluidised bed of mordenite catalyst maintained at the required temperature, such as in the range 250 to 400° C., such as 275 to 350° C. The process is typically carried out at a total reaction pressure in the range 1 to 100 bar.

If the carbonylation reaction is to be conducted substantially in the absence of water, it is preferred that the mordenite catalyst is dried prior to use. The mordenite may be dried, for example by heating to a temperature of 400 to 500° C.

Suitably, the mordenite catalyst is activated immediately before use in the carbonylation reaction by heating the mordenite catalyst at elevated temperature for at least one hour under flowing nitrogen, carbon monoxide, hydrogen or mixtures thereof.

The carbon monoxide employed in the carbonylation process may be substantially pure carbon monoxide, for example, carbon monoxide typically provided by suppliers of industrial gases, or it may contain impurities that do not interfere with the conversion of the dimethyl ether to methyl acetate, such as nitrogen, helium, argon, methane and/or carbon dioxide.

The carbonylation process of the present invention may be conducted in the presence of hydrogen. Thus, the carbon monoxide feed may contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide. The molar ratio of carbon monoxide:hydrogen may be in the range 1:3 to 15:1. The molar ratio of carbon monoxide to dimethyl ether or dimethyl carbonate may be in the range 1:1 to 99:1. The molar ratio of carbon monoxide to methanol is suitably in the range 1:1 to 60:1.

The carbonylation process may be conducted as a batch or as a continuous process, preferably as a continuous process.

In the Figures.

The invention is now illustrated with reference to the following Examples.

General Reaction Method 1

The carbonylation of dimethyl ether (DME) in the presence of a mordenite zeolite catalyst was carried out in a pressure flow reactor unit consisting of 16 identical reactors of the type described in WO 2005063372. Prior to the loading of a catalyst sample into the reactor, a ca. 5 cm bed of steatite of sieve fraction of 100-350 µm was placed in the respective catalyst sample holder. A ca. 5 cm zone of corundum of sieve fraction of 125-160 µm was placed on top of the steatite bed. On a dry mass basis (determined by loss on ignition of the relevant sample measured by heating the sample from room temperature to 600° C. at a ramp rate of ca. 30° C. per minute) a 0.625 g (ca. 1 ml) sample of a catalyst was then placed on top of the corundum bed. The catalyst sample was covered by a ca. 5 cm corundum bed of a particle size of 125-160 µm. A ca. 5 cm zone of steatite of sieve fraction of 100-350 µm was placed on top of the corundum bed. Every zone was concreted via hitting or vibrating to get a stable bed and a defined starting height of the catalyst zone. The catalyst sample was then pressurised to the desired reaction pressure of 70 bar with CO/$H_2$ 4/1 mixture at a flow rate of 4 l/h. The catalyst was then heated at 0.5° C./min to a holding temperature of 220° C., where it was held for a dwell time of 3 hours. Subsequently the temperature was ramped to 300° C. at 0.5° C./min, again followed by a further dwell time of 3 hours. The gas feed was then switched to a mixture of carbon monoxide hydrogen and DME with a CO/$H_2$/DME ratio of 72/18/10 at a flow rate of 4 l/h, with the DME fed at 0.38 l/h as a vapour, to obtain a CO/$H_2$/DME ratio in the total feed of 72/18/10 on a molar basis. In addition, $N_2$ was introduced at a variable rate of 0-50 ml/min to equalise the pressure swings between the 16 reactor exits. The exit stream from each test reactor was passed to a gas chromatograph to determine the concentration of reactants and carbonylation products.

Preparation of Cu(55)Mordenite

H-mordenite (100.1 g) with a silica to alumina ratio of 20 (ex Süd-Chemie) was weighed into a 1 liter round bottomed flask with a stirrer bar. 18.1 g of copper (II) nitrate hemipentahydrate (98% ACS reagent grade) was dissolved in a minimum amount of deionised water. This solution was then added to the mordenite together with sufficient deionised water (ca. 150 mL) to give a mobile slurry. The top of the flask was covered loosely and the flask left to stir overnight. The zeolite was then dried under reduced vacuum using a rotary evaporator before being dried in an oven at 90° C. for 1-2 hours. The zeolite was then calcined in a muffle oven (oven volume=18 L) under a static atmosphere of air at 500° C. for 3 hours after two drying stages of 90° C. for 2 hours and 110° C. for 2 hours. The zeolite (ca. 0.75 g batches) was then compacted at 10 tonnes in a 13 mm die set using a pneumatic press, and crushed and sieved to a particle size fraction of 125 to 160 microns. The zeolite (Cu(55)-Mordenite) had a Cu loading of ca. 55 mole % relative to Al contained in the mordenite Preparation of H-Mordenite H-mordenite with a silica to alumina ratio of 20 (ex Süd-Chemie) was calcined in a muffle oven (oven volume=18 L) under a static atmosphere of air at 500° C. for 3 hours after two drying stages of 90° C. for 2 hours and 110° C. for 2 hours. The zeolite was then compacted (ca. 0.75 g at a time) at 10 tonnes in a 13 mm die set using a pneumatic press, and crushed and sieved to a particle size fraction of 125 to 160 microns.

EXAMPLES 1 and 2

The apparatus and method described in General Reaction Method 1 above was used to prepare methyl acetate by the carbonylation of dimethyl ether in the presence of Cu-mordenite catalyst (Example 1) and H-mordenite catalyst (Example 2). In Examples 1 and 2 the reaction was allowed to continue for 98 hours under conditions of 300° C., 70 bar, a gas hourly space velocity (GHSV) of 4000 h$^{-1}$ and with a CO/H$_2$/DME ratio in the total feed of 72/18/10 on a molar basis. After 98 hours each catalyst was subjected to a first regeneration according to the following procedure:

After 98 hours total reaction time the CO/H$_2$/DME feed was switched to N$_2$ and the reactors purged for 30 minutes. The catalysts were then treated at 300° C. and 70 bar total pressure with a gas stream containing 1 volume % O$_2$ (0.7 bar) and 99 volume % N$_2$ for 8 hours at a GHSV of 4000 h$^{-1}$. After that the oxygen content in the gas stream was increased to 2 volume % (1.4 bar) (with 98 volume % N$_2$) and the catalysts were treated for a further 10 hours at 70 bar total pressure and 300° C.

After the first regeneration the reactors were purged for 30 minutes with N$_2$. The DME carbonylation reaction was then re-started under conditions of 300° C., 70 bar total pressure, a GHSV of 4000 h$^{-1}$ with a feedstock ratio of CO/H$_2$/DME 72/18/10. The reaction was then allowed to continue for a further 53 hours (172 hours total) and the CO/H$_2$/DME feed was switched to N$_2$ and the reactors purged for 30 minutes.

The catalyst was then subjected to a second regeneration using the same procedure as in the first regeneration.

After the second regeneration the reactors were purged for 30 minutes with N$_2$. The DME carbonylation reaction was then re-started under conditions of 300° C., 70 bar, a GHSV of 4000 h$^{-1}$ with a feedstock ratio of CO/H$_2$/DME 72/18/10. The reaction was then allowed to continue for a further 64 hours.

Figure 1:
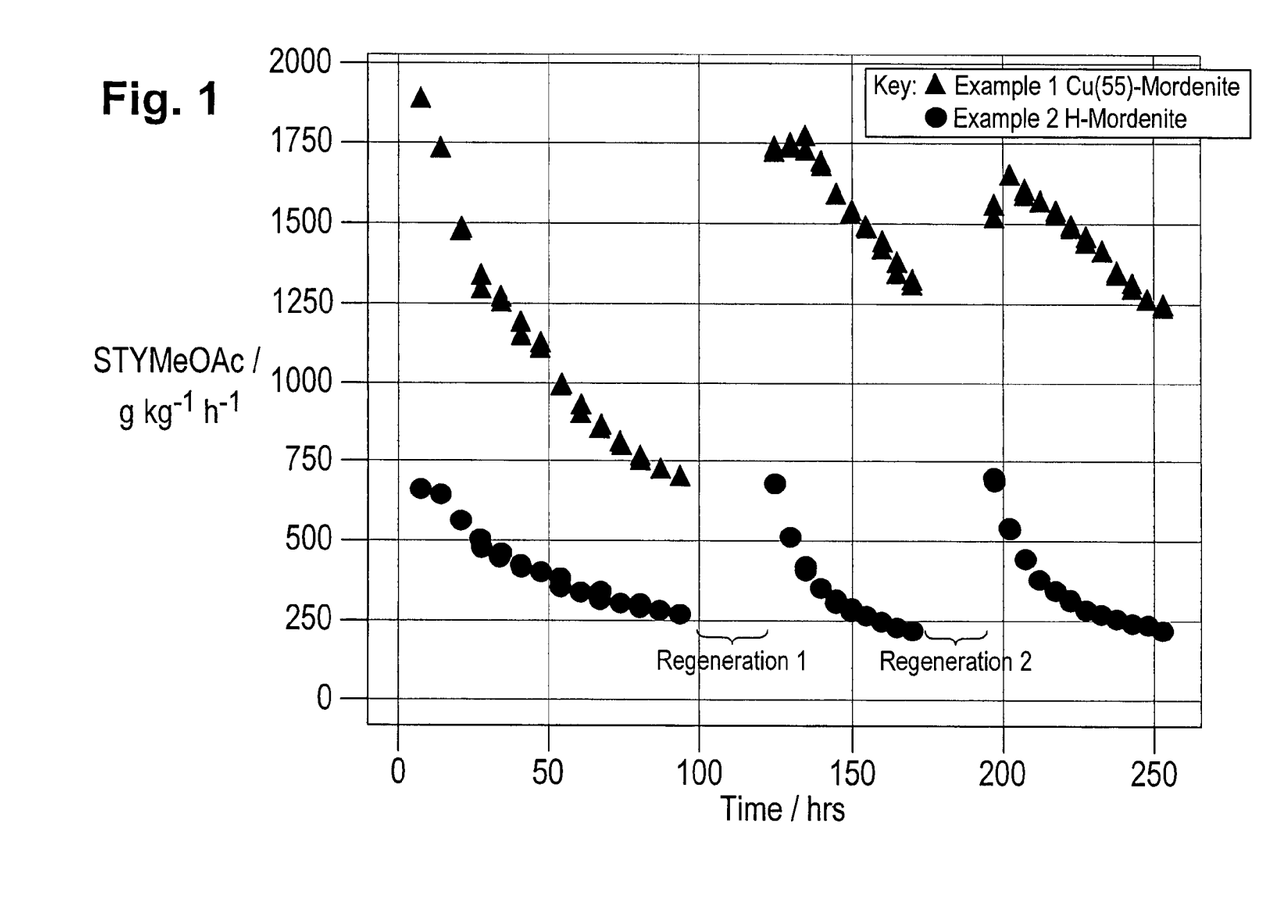
FIG. 1 depicts the STY to methyl acetate product in g $kg^{-1}$ $h^{-1}$ versus time on stream for H-mordenite and Cu-mordenite catalysts before and after 2 regenerations at 300° C.
Figure 2:
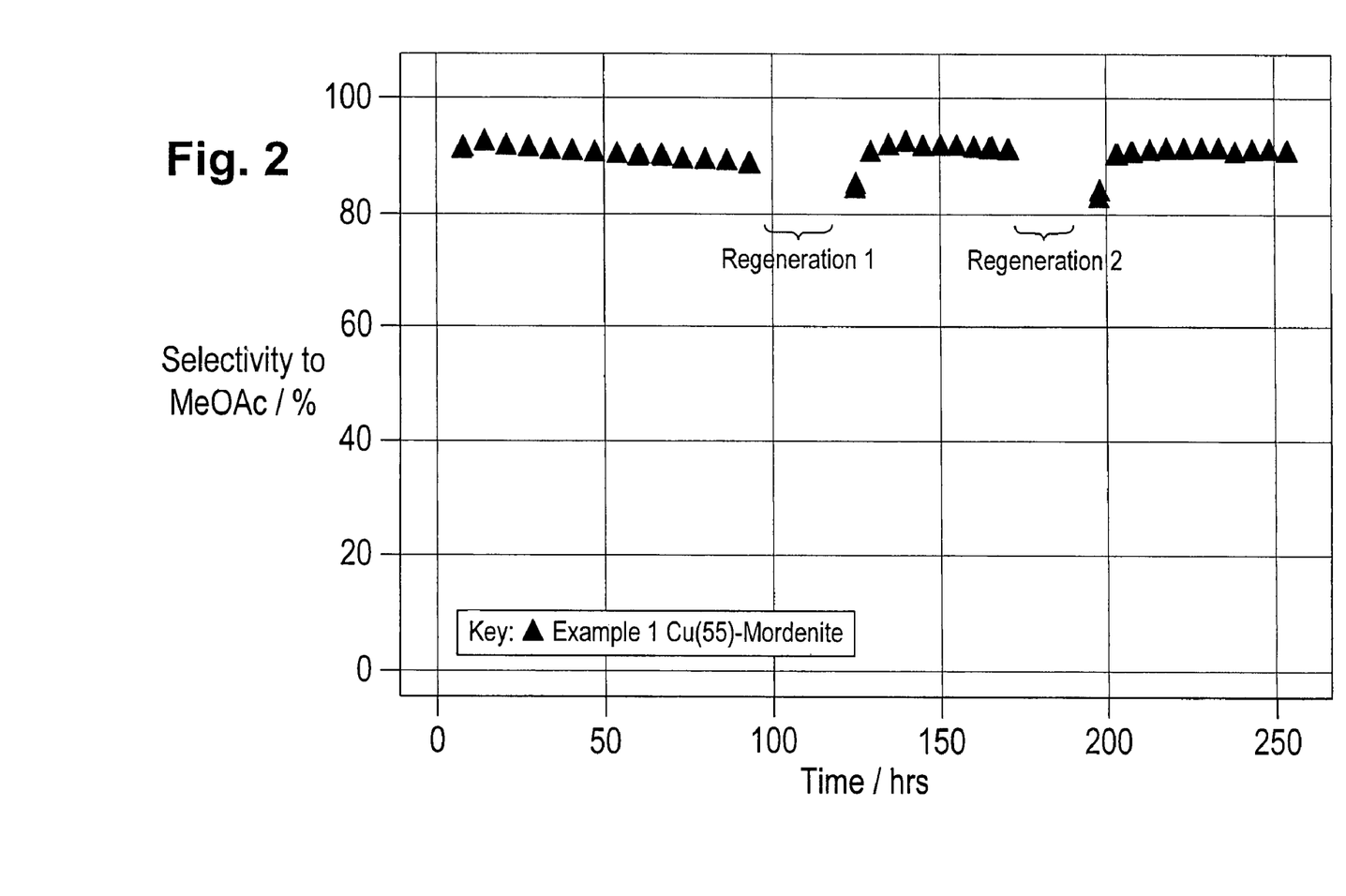
FIG. 2 depicts Selectivity to methyl acetate product versus time on stream for Cu-mordenite before and after 2 regenerations at 300° C.

The results for Examples 1 and 2 are given in FIGS. 1 and 2. FIG. 1 shows the initial carbonylation activity of the H-Mordenite catalyst to be fully restored after treatment with 1 volume % (0.7 bar) and 2 volume % (1.4 bar) O$_2$ at 300° C. FIG. 1 also shows the initial carbonylation activity of the Cu(55)-Mordenite catalyst to be largely restored after treatment with 1 and 2 volume % O$_2$ at 300° C. Furthermore, after the initiation period when the DME feed is first introduced to the carbonylation reactor, FIG. 2 shows the initial selectivity of the Cu(55)-Mordenite catalyst to MeOAc (based upon DME converted) to be restored to its original level after regeneration of the catalyst with 1 and 2 volume % (0.7 and 1.4 bar respectively) O$_2$ at 300° C.

EXAMPLES 3 and 4

A Cu(55) mordenite and H-mordenite prepared as described above were used as the catalyst in Examples 3 and 4 respectively. Each catalyst was used in the carbonylation of dimethyl ether to prepare methyl acetate by the procedure described in General Reaction Method 1 except that the carbon monoxide, hydrogen, dimethyl ether gas feed had a molar ratio of 76/19/5 and a flow rate of 4 l/h, with a dimethyl ether flow rate of 0.196 l/h (as a vapour) to obtain a CO/H$_2$/DME ratio in the total feed of 76/19/5 on a molar basis. The reaction was allowed to continue for 123 hours under conditions of 300° C., 70 bar total pressure, a GHSV of 4000 h$^{-1}$ and a CO/H$_2$/DME ratio in the total feed of 76/19/5 on a molar basis. After 129 hours total reaction time, the CO/H$_2$/DME feed was switched to N$_2$ and the reactors purged for 30 minutes. After purging with N$_2$ the temperature of the reactors was dropped to 250° C. and each catalyst was subjected to a first regeneration as follows:

The catalysts were regenerated at 250° C. and 70 bar total pressure with a gas stream containing 1 volume % (0.7 bar) O$_2$ and 99 volume % N$_2$ for 13.5 hours at a GHSV of 4000 h$^{-1}$. The O$_2$ content in the gas stream was then increased to 2 volume % (1.4 bar) (with 98 volume % N$_2$) and the catalysts were treated for a further 4 hours at 70 bar total pressure and 250° C.

After the first regeneration the reactors were purged for 30 minutes with N$_2$ and then heated at 3° C./min to 300° C. The carbonylation reaction was then re-started under conditions of 300° C., 70 bar total pressure and a GHSV of 4000 h$^{-1}$ with a CO/H$_2$/DME molar ratio of 76/19/5. The reaction was allowed to continue for a further 48 hours (197 hours total), after which time, the CO/H$_2$/DME feed was switched to N$_2$ and the reactors purged for 30 minutes. After purging with N$_2$ the temperature of the reactors was dropped to 250° C. and the catalysts were regenerated for a second time by repeating the procedure employed in the first regeneration.

After the second regeneration the reactors were purged for 30 minutes with N$_2$ and then heated at 3° C./min to 300° C. The carbonylation reaction was re-started under conditions of 300° C., 70 bar, a GHSV of 4000 with a CO/H$_2$/DME molar ratio of 76/19/5. The reaction was allowed to continue for a further 69 hours (287 hours total reaction time) after which time, the CO/H$_2$/DME feed was switched to N$_2$ and the reactors purged for 30 minutes. After purging with N$_2$ the temperature of the reactors was dropped to 250° C. The catalysts were regenerated for a third time by treating the catalysts at 300° C. and 70 bar total pressure with a gas stream containing 1 volume % $O_2$ and 99 volume % $N_2$ for 13.5 hours at a GHSV of 4000 $h^{-1}$. The $O_2$ content in the gas stream was then increased to 2 volume % (98 volume % $N_2$) and the catalysts were treated for a further 4 hours at 70 bar total pressure, a GHSV of 4000 $h^{-1}$ and 250° C. The reactors were then heated at 3° C./min to 300° C., and the catalysts treated for a further 6 hours with a gas containing 2 vol % $O_2$ and 98 vol % $N_2$ at a GHSV of 4000 $h^{-1}$. After the third regeneration the reactors were purged for 30 minutes with $N_2$. The carbonylation reaction was re-started under conditions of 300° C., 70 bar total pressure and a GHSV of 4000 $h^{-1}$ with a CO/$H_2$/DME molar ratio of 76/19/5. The reaction was allowed to continue for a further 46 hours.

Figure 3:
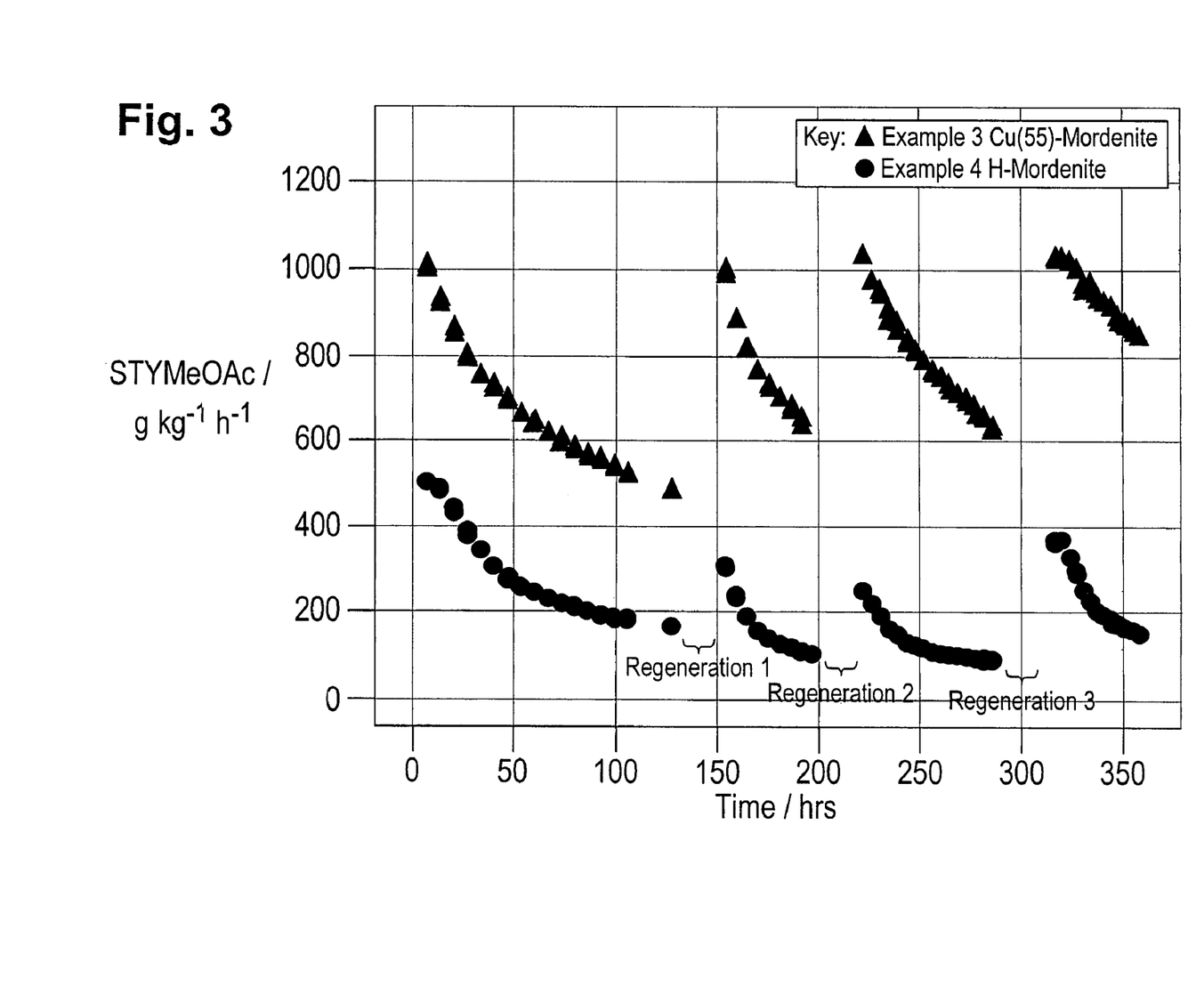
FIG. 3 depicts the STY to methyl acetate product in g $kg^{-1}$ $h^{-1}$ versus time on stream for Cu-mordenite and H-mordenite before and after 2 regenerations at 250° C. and a $3^{rd}$ regeneration at 300° C.
Figure 4:
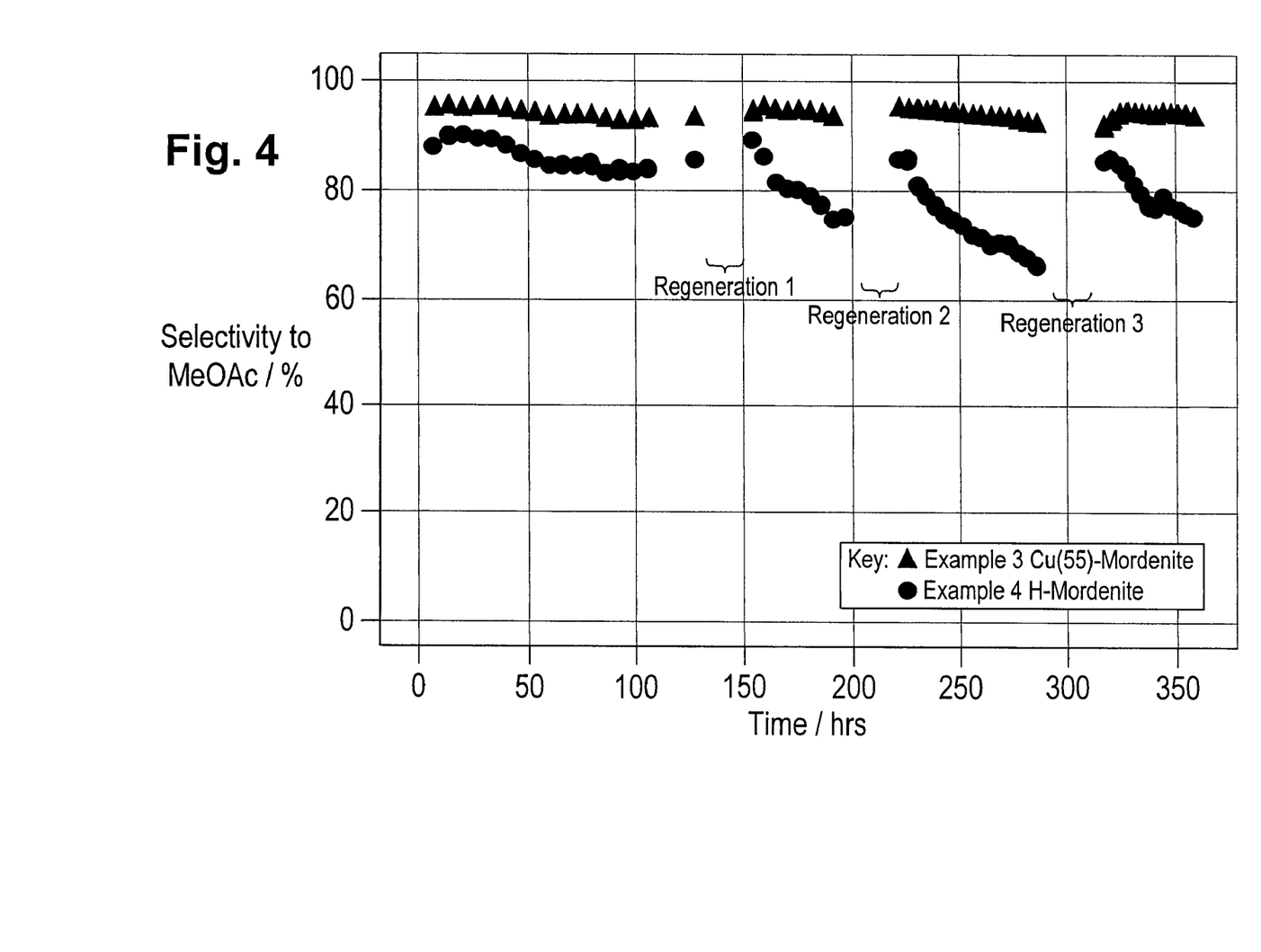
FIG. 4 depicts Selectivity to methyl acetate product versus time on stream for Cu-mordenite and H-mordenite before and after 2 regenerations at 250° C. and a $3^{rd}$ regeneration at 300° C.

The results for Examples 3 and 4 are given in FIG. 3 and FIG. 4. FIG. 3 shows the initial carbonylation activity of the Cu(55)-Mordenite to be fully restored after 2 regenerations of the catalyst with 1 and 2 volume % $O_2$ at 250° C. Catalyst activity data after regeneration 3 shown in FIG. 3 also illustrates that after first treating the H-Mordenite catalysts with $O_2$ at 250° C. it is beneficial to further treat the catalyst with $O_2$ at 300° C. FIG. 4 shows that the selectivity of the catalysts after each regeneration is improved compared to the selectivity immediately prior to regeneration.

EXAMPLE 5

Preparation of Ag(55)-mordenite $NH_4$-mordenite (25.05 g) with a silica to alumina ratio of 20 (ex Zeolyst) was weighed into a 250 mL round bottomed flask with a stirrer bar. 3.2726 g of silver (I) nitrate was dissolved in a minimum amount of deionised water. This solution was then added to the mordenite along with sufficient deionised water (ca. 150 mL) to give a mobile slurry. The top of the flask was covered loosely and the flask stirred overnight. The zeolite was then dried under reduced vacuum using a rotary evaporator before being dried in an oven at 90° C. for 1-2 hours. The zeolite was then calcined in a muffle oven (oven volume=18 L) under a static atmosphere of air at 500° C. for 3 h after two drying stages of 90° C. for 2 hours and 110° C. for 2 hours. The zeolite (ca. 0.75 g batches) was then compacted at 10 tonnes in a 13 mm die set using a pneumatic press, and crushed and sieved to a particle size fraction of 125 to 160 microns. The zeolite (Ag(55)-MOR) had a Ag loading of ca. 55 mole % relative to Al contained in the mordenite. ICP spectroscopic analysis showed the mordenite catalyst to contain 8.2% Ag and 3.6% Al on a % by weight basis, equivalent to a Ag loading of 57 mole % relative to Al.

Ag-mordenite as prepared above was used as the catalyst in the carbonylation of dimethyl ether to prepare methyl acetate. The method and apparatus of General Reaction Method 1 was used. The reaction was allowed to continue for 97 hours under conditions of 300° C., 70 bar total pressure, a gas GHSV of 4000 $h^{-1}$ and with a CO/$H_2$/DME molar ratio in the total feed of 72/18/10. After 97 hours the catalyst was subjected to a first regeneration as follows:

After 97 hours total reaction time the CO/$H_2$/DME feed was switched to $N_2$ and the reactors purged for 30 minutes. After purging with $N_2$ the temperature of the reactors was dropped to 250° C. The catalysts were then treated at 250° C. and 70 bar total pressure with a gas stream containing 1 volume % $O_2$ and 99 volume % $N_2$ for 13.5 hours at a GHSV of 4000 $h^{-1}$. The $O_2$ content in the gas stream was then increased to 2 volume % (98 volume % $N_2$) and the catalysts were treated for a further 4 hours at 70 bar total pressure and 250° C.

After the first regeneration the reactors were purged for 30 minutes with $N_2$ and then heated at 3° C./min to 300° C. The carbonylation reaction was re-started under conditions of 300° C., 70 bar total pressure and a GHSV of 4000 $h^{-1}$ with a CO/$H_2$/DME molar ratio of 72/18/10. The reaction was allowed to continue for a further 50 hours (171 hours total reaction time), after which time the CO/$H_2$/DME feed was switched to $N_2$ and the reactors purged for 30 minutes. After purging with $N_2$ the temperature of the reactors was dropped to 250° C. and the catalyst was subjected to a second regeneration by repeating the method of the first regeneration.

After the second regeneration the reactors were again purged for 30 minutes with $N_2$ and then heated at 3° C./min to 300° C. The carbonylation reaction was re-started under conditions of 300° C., 70 bar, a GHSV of 4000 $h^{-1}$ with a CO/$H_2$/DME molar ratio of 72/18/10. The reaction was allowed to continue for a further 71 hours (to a total of 265 hours), after which time the CO/$H_2$/DME feed was switched to $N_2$ and the reactors purged for 30 minutes. After purging with $N_2$ the temperature of the reactors was dropped to 250° C. The catalyst was regenerated for a third time by repeating the method of the first regeneration.

After the third regeneration the reactors were purged for 30 minutes with $N_2$ and then heated at 3° C./min to 300° C. The carbonylation reaction was re-started under conditions of 300° C., 70 bar, a GHSV of 4000 with a CO/$H_2$/DME molar ratio of 72/18/10. The reaction was allowed to continue for a further 48 hours (to 339 hours total reaction time), after which time, the CO/$H_2$/DME feed was switched to $N_2$ and the reactors purged for 30 minutes. After purging with $N_2$ the temperature of the reactors was dropped to 250° C. and the catalyst was regenerated for a fourth time by repeating the method of the first regeneration.

After the fourth regeneration the reactors were purged for 30 minutes with $N_2$ and then heated at 3° C./min to 300° C. The carbonylation reaction was re-started under conditions of 300° C., 70 bar, a GHSV of 4000 $h^{-1}$ with a CO/$H_2$/DME molar ratio of 72/18/10. The reaction was then allowed to continue for a further 69 hours.

Figure 5:
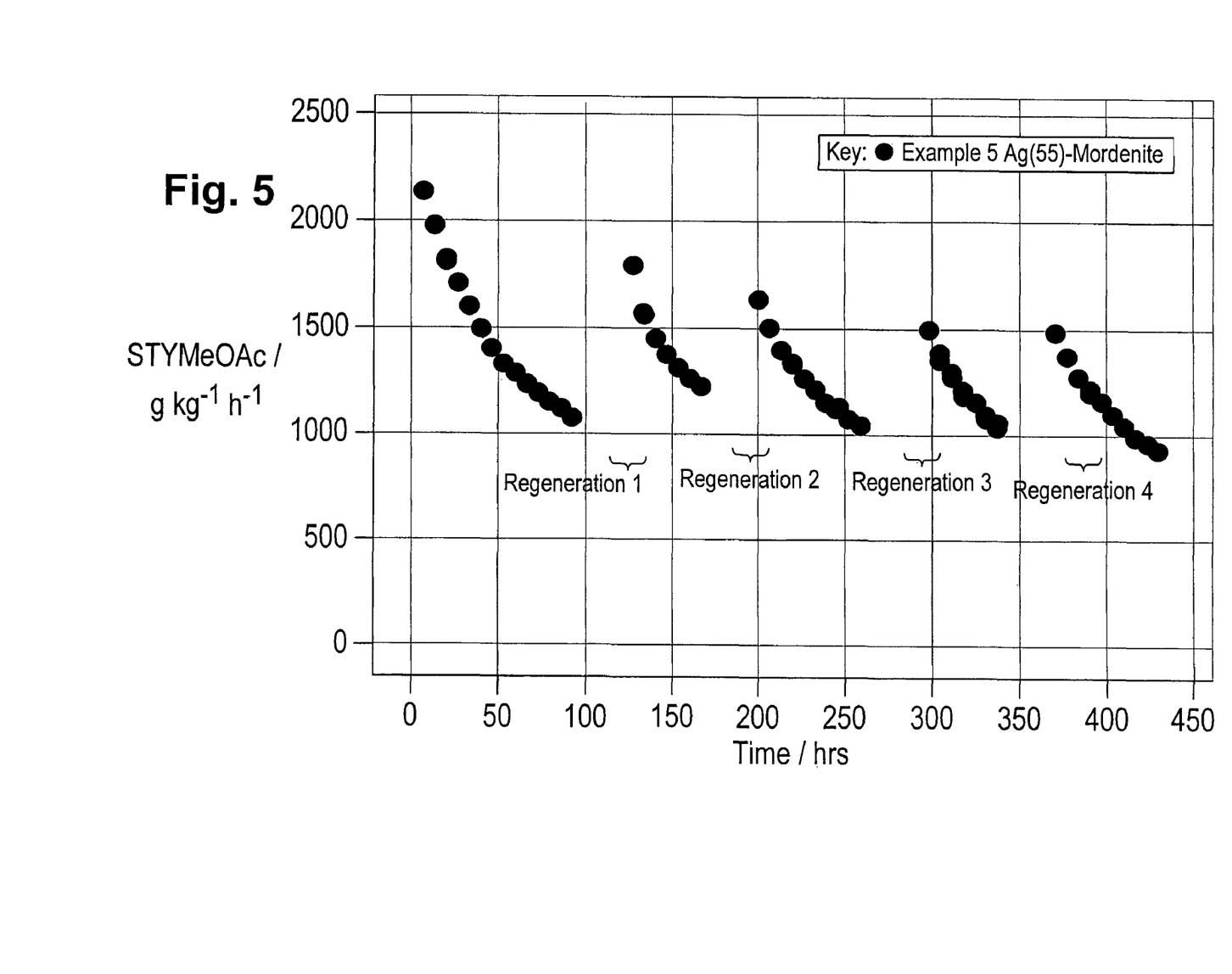
FIG. 5 depicts the STY to methyl acetate product in g $kg^{-1}$ $h^{-1}$ versus time on stream for Ag-mordenite before and after 4 regenerations at 250° C.
Figure 6:
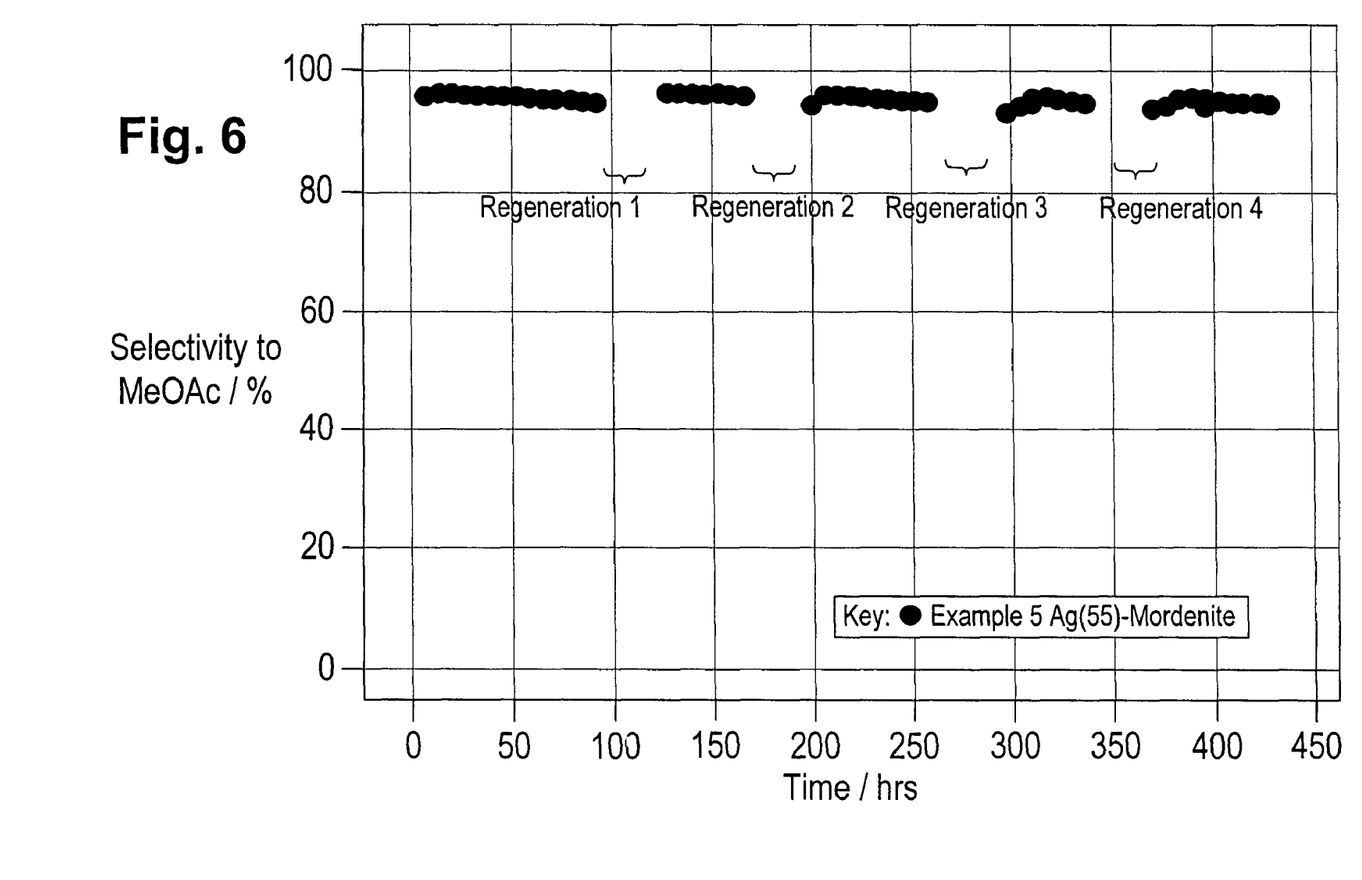
FIG. 6 depicts Selectivity to methyl acetate product versus time on stream for Ag-mordenite before and after 4 regenerations at 250° C.

The results for Example 5 are given in FIGS. 5 and 6. FIG. 5 shows the initial carbonylation activity of the Ag(55)-Mordenite catalyst to be substantially restored after the first regeneration of the catalyst with 1 and 2 volume % $O_2$ at 250° C. FIG. 6 shows that the selectivity of the catalyst after each regeneration is maintained at or above the selectivity achieved immediately prior to each regeneration.

EXAMPLE 6

Preparation of Cu(55)-Mordenite

H-Mordenite (80 g) with a silica to alumina ratio of 20 (ex Süd Chemie) and 14.29 g of copper (II) nitrate hemipentahydrate (98% ACS reagent grade) were weighed into a 500 mL round bottomed flask with a stirrer bar. Sufficient deionised water (ca. 150 mL) was added to the flask to obtain a thick slurry. The top of the flask was loosely covered and the flask left to stir overnight. The zeolite was then dried under reduced vacuum using a rotary evaporator before being dried in an oven at 90° C. for 1 hour. The zeolite was then calcined in a muffle oven (oven volume=18 L) under a static atmosphere of air. The temperature was increased from room temperature to 90° C. at a ramp rate of ca. 3° C./min and then held at this temperature for 2 hours. The temperature was then increased to 110° C. at a ramp rate of ca. 1° C./min and held at this temperature for 2 hours before finally being increased to a temperature of 500° C. at a ramp rate of ca. 3° C./min and held at this temperature for 5 hours. The zeolite was then compacted at 12 tonnes in a 33 mm die set using a Specac Press, and then crushed and sieved to a particle size fraction of 212 to 335 microns. The Cu-mordenite had a Cu loading of 55 mole % of the amount of Al contained in the zeolite.

Preparation of Ag(55)-Mordenite

Ag-mordenite was prepared by the procedure as described above for the preparation of Cu-mordenite except that the copper (II) nitrate was replaced by 10.47 g of silver nitrate (99% ACS reagent grade). The Ag-mordenite so prepared had a Ag loading of 55 mole % of the amount of Al contained in the mordenite.

Preparation of H-Mordenite

H-Mordenite (80 g) with a silica to alumina ratio of 20 (ex Süd Chemie) was calcined, compacted, crushed and sieved in accordance with the procedures described in the preparation of Cu-mordenite above.

Carbonylation Reaction

Each of the catalysts, Cu-mordenite, Ag-mordenite and H-mordenite was used to catalyse the carbonylation of dimethyl ether to methyl acetate using the following apparatus and procedure. The carbonylation reaction was carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. Into each tube 50 micro liters of catalyst (designed to give a GHSV of 4000 hr$^{-1}$) was loaded onto a metal sinter having a pore size of 20 micrometers. The catalyst samples were heated at a ramp rate of 5° C./min. to 100° C. at atmospheric pressure under 98.6 mole % nitrogen and 1.4 mole % helium at a flow rate of 3.4 mL/min, and held at this temperature for 1 hour. The reactor was then pressurised to 70 barg with a gas mixture comprising 98.6 mole % nitrogen and 1.4 mole % helium and the system held at this condition for 1 hour. The gas feed was then changed from the nitrogen and helium mix to a mixture comprising 63.1 mole % carbon monoxide, 15.8 mole % hydrogen, 19.7 mole % nitrogen and 1.4 mole % helium at a gas flow rate of 3.4 mL/min, and the reactors were heated at a ramp rate 3° C./min. to a temperature of 300° C. The system was then held at this condition for 3 hours. At this point catalyst activation is considered complete, and the gas feed was changed to a mixture comprising 63.1 mole % carbon monoxide, 15.8 mole % hydrogen, 14.8 mole % nitrogen, 1.4 mole % helium and 4.9 mole % dimethyl ether at a gas flow rate of 3.4 mV min. The reaction was allowed to continue for 161.2 hours at which stage the gas feed was changed to mixture comprising 98.6 mole nitrogen and 1.4 mole % helium at a gas flow rate of 3.4 ml/min, and all of the reactors were allowed to cool down to 100° C. The system was held under these conditions for 30 minutes and then regeneration of the catalysts was conducted under the conditions in the following table. In all cases the gas flow was 3.4 ml/min at a pressure of 70 barg.

| Nitrogen mole % | Air* mole % | Helium mole % | Block 1 deg C. | Block 2 deg C. | Block 3 deg C. | Block 4 deg C. | Time hours |
|---|---|---|---|---|---|---|---|
| 78.9 | 19.7 | 1.4 | 250 | 300 | 350 | 400 | 5.8 |
| 59.2 | 39.4 | 1.4 | 250 | 300 | 350 | 400 | 5.8 |
| 19.7 | 78.9 | 1.4 | 250 | 300 | 350 | 400 | 5.8 |

*Air = 20.95 mol % oxygen, 78.05 mol % nitrogen and 1 mol % other gases, mostly argon.

Figure 7:
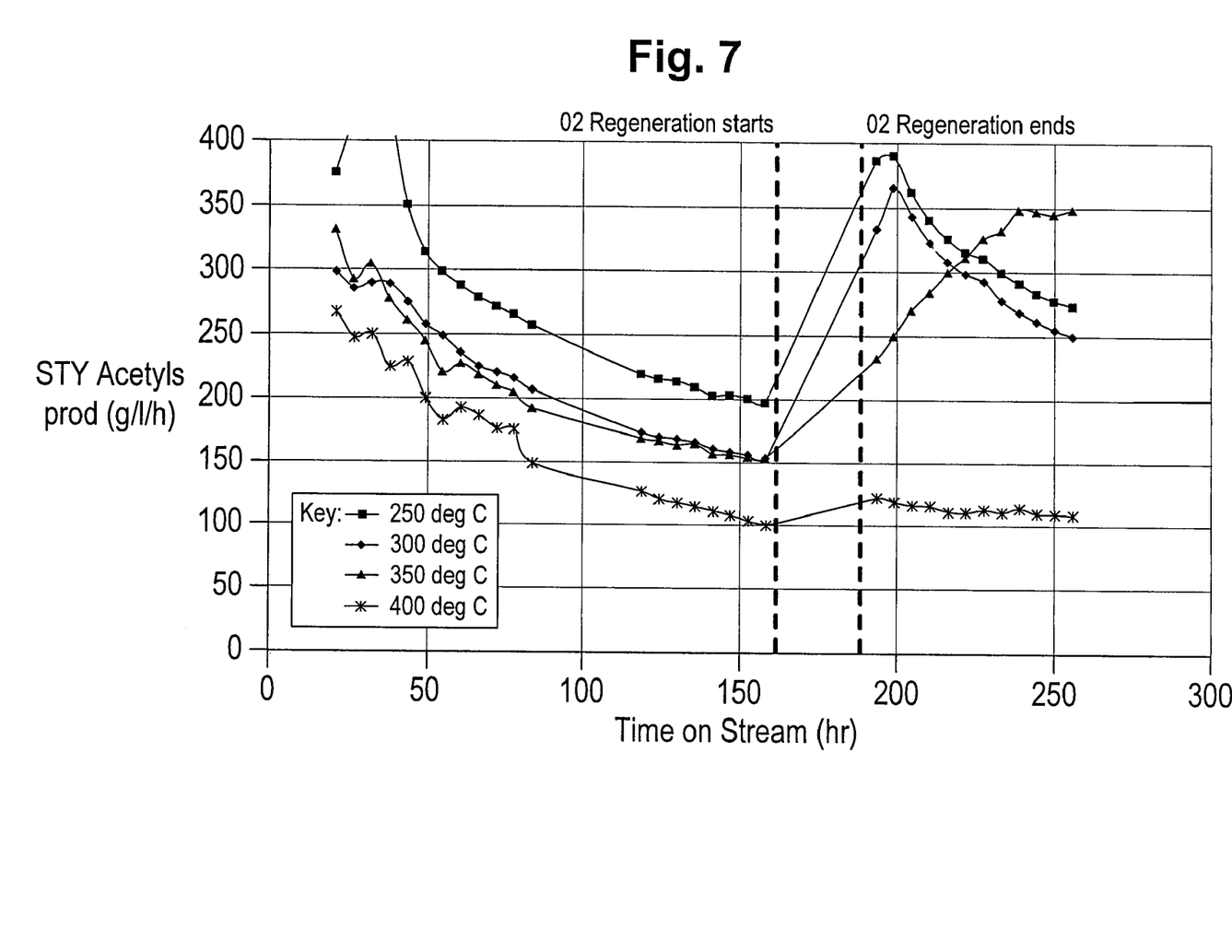
FIG. 7 depicts the STY to acetyls product in g $l^{-1}$ $h^{-1}$ versus time on stream for Cu-mordenite before and after regeneration at 250° C., 300° C., 350° C. and 400° C.
Figure 8:
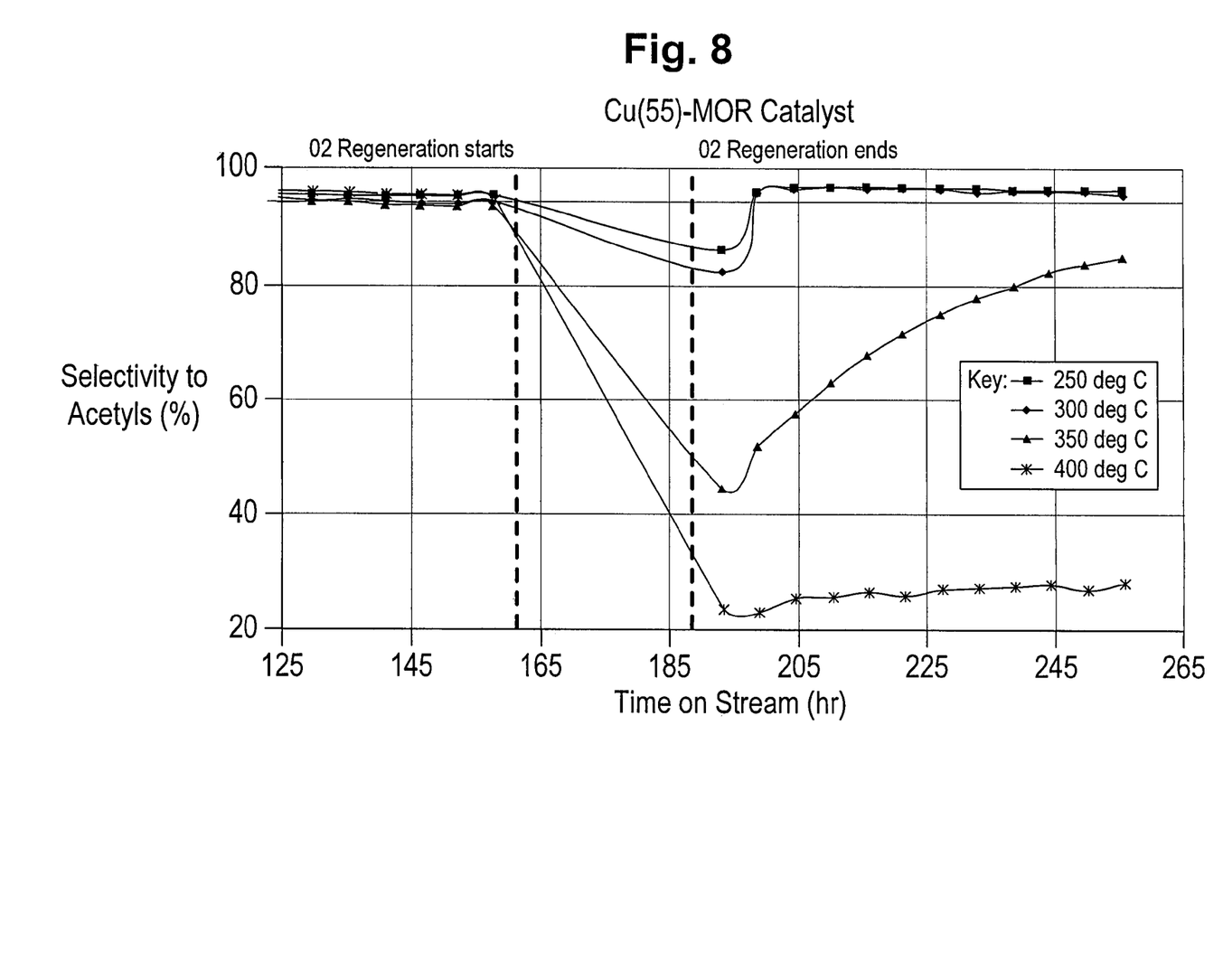
FIG. 8 depicts Selectivity to acetyls product versus time on stream for Cu-mordenite before and after regeneration at 250° C., 300° C., 350° C. and 400° C.
Figure 9:
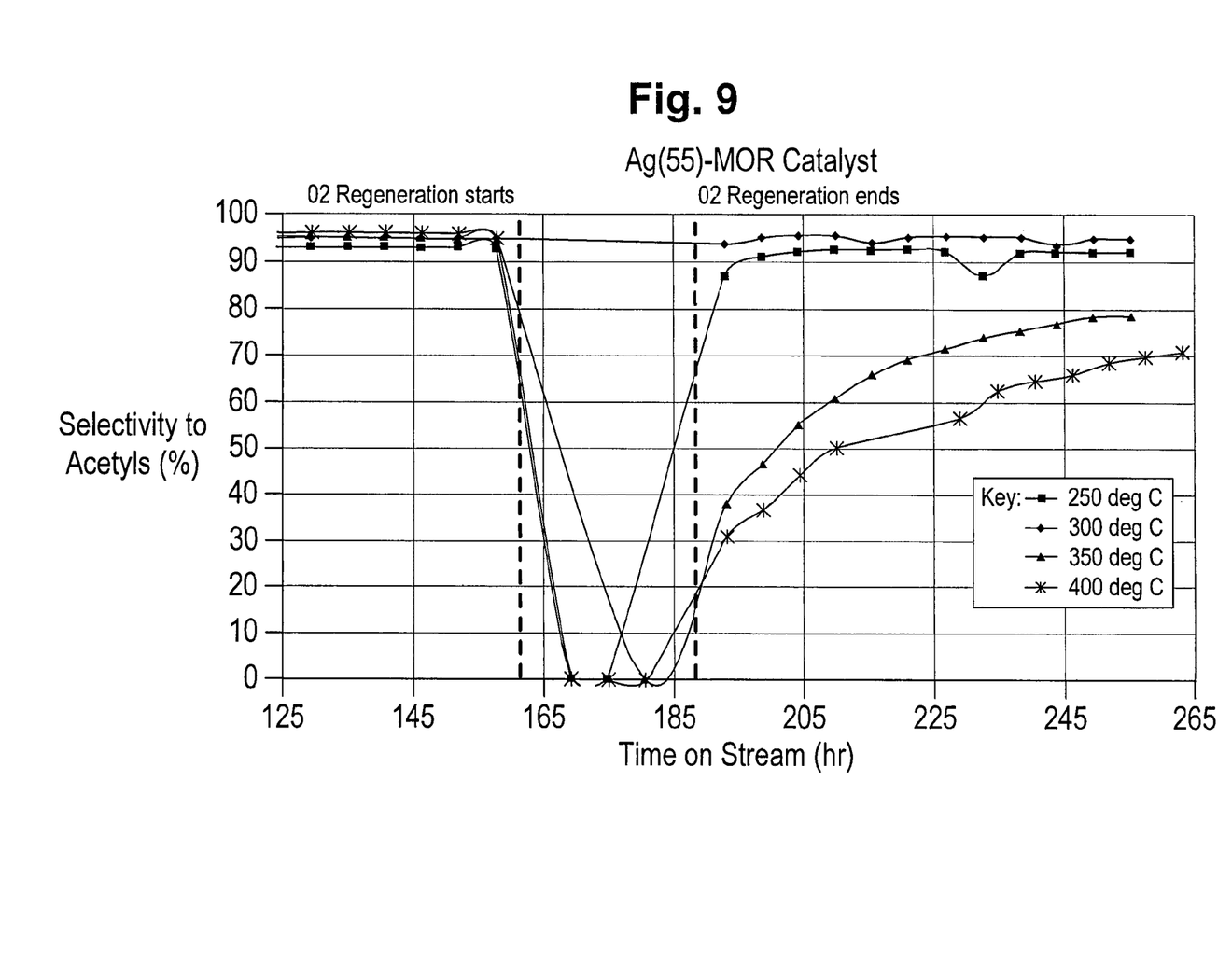
FIG. 9 depicts Selectivity to acetyls product versus time on stream for Ag-mordenite before and after regeneration at 250° C., 300° C., 350° C. and 400° C.
Figure 10:
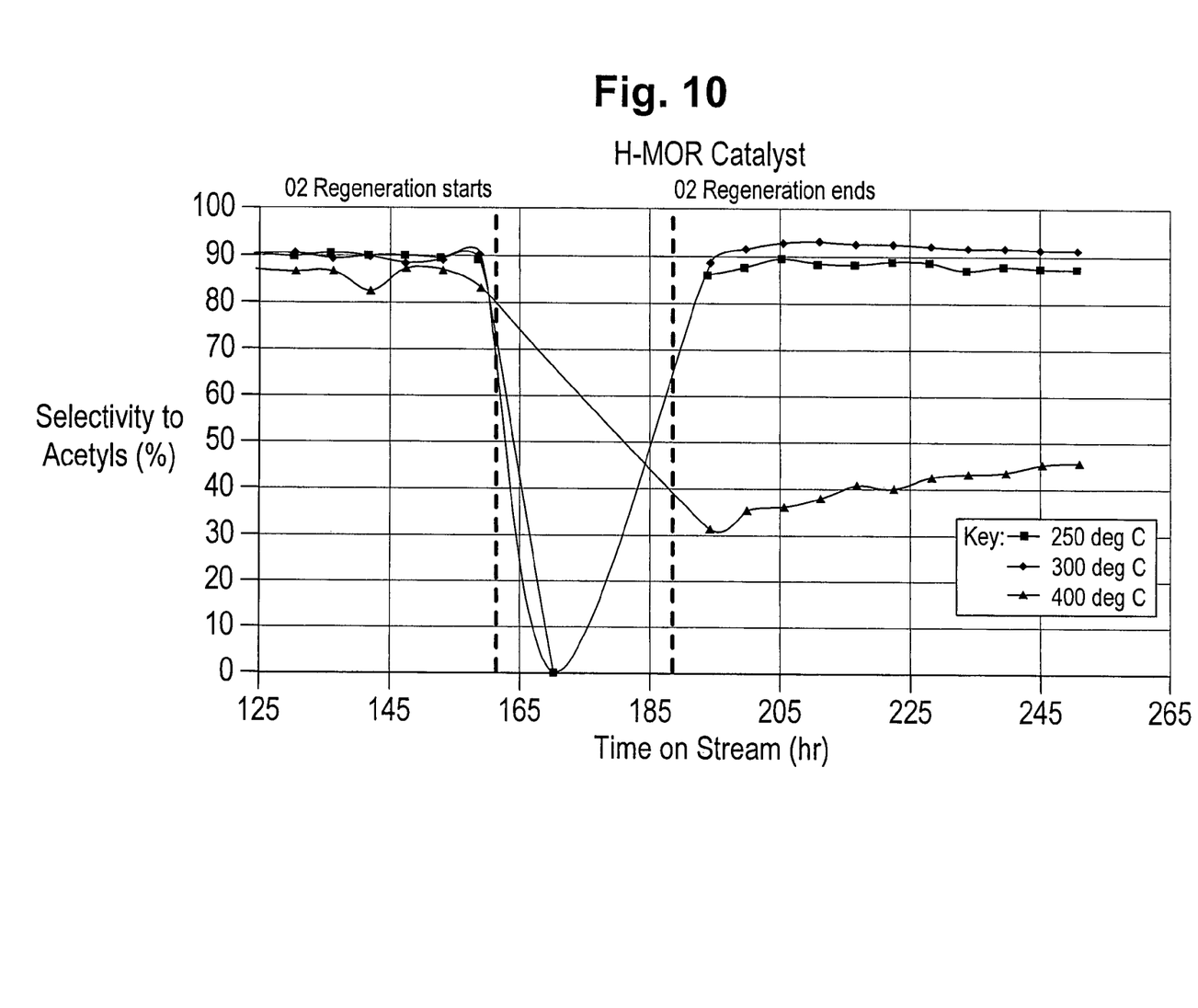
FIG. 10 depicts Selectivity to acetyls product versus time on stream for H-mordenite before and after regeneration at 250° C., 300° C. and 400° C.

Once this was complete, the gas feed was changed to a mixture comprising 98.6 mole % nitrogen and 1.4% helium and the reactor were allowed to cool down to 100° C. The system was held at this condition for 30 minutes before the reactors were heated to 300° C. and the gas feed changed to a mixture comprising 63.1 mole % carbon monoxide, 15.8 mole % hydrogen, 19.7 mole % nitrogen and 1.4 mole % helium at a gas flow rate of 3.4 mL/min. The system was held at this condition for 3 hours before the carbonylation reaction was re-started by changing the feed to a mixture comprising 63.1 mole % carbon monoxide, 15.8 mole % hydrogen, 14.8 mole % nitrogen, 1.4 mole % helium and 4.9 mole % dimethyl ether. The exit stream from the reactor was passed to two gas chromatographs. One of these was a Varian 4900 micro GC with three columns (Molecular sieve 5A, Porapak® Q, and CP-Wax-52) each quipped with a thermal conductivity detector. The other was an Interscience Trace GC with two columns (CP-Sil 5 and CP-Wax 52) each equipped with a flame ionisation detector. The STY to Acetyls products (g/l/h) is shown in FIG. 7 and Selectivity to Acetyls products is shown in FIGS. 8 to 10. Selectivity is defined as the molar selectivity of the reaction of the methoxy group in the dimethyl ether (DME) feed to the products acetic acid (AcOH) and methyl acetate (MeOAc).

Selectivity=([MeOAc]out+[AcOH]out)/([DME]in−
[DME]out−0.5*[MeOH]out−0.5*[MeOAc]out)
*100

FIG. 7 shows that the activity of the Cu-mordenite catalyst is restored after regeneration.

FIG. 8 shows that shortly after regeneration at 250 and 300° C. the selectivity of Cu-mordenite catalyst has been substantially restored to the selectivity achieved immediately prior to regeneration. In comparison the selectivity of Cu-mordenite regenerated at 350 and 400° C. has been dramatically reduced, and even though the selectivity of the catalyst regenerated at 350° C. is recovering it is still not within 10% of the selectivity of the catalyst prior to the regeneration treatment after over 60 hours of operation.

FIG. 9 shows that regeneration at 350° C. and 400° C. adversely affects the selectivity of the Ag-mordenite catalyst and FIG. 10 shows that regeneration at 400° C. adversely affects the selectivity of the H-mordenite catalyst.

The invention claimed is:

1. A process for the production of at least one of methyl acetate and acetic acid by the carbonylation in a reactor of a carbonylatable reactant selected from methanol, dimethyl ether and dimethyl carbonate with carbon monoxide and hydrogen in the presence of a mordenite zeolite catalyst in which process the catalyst is regenerated in-situ by contacting the catalyst with a regenerating gas comprising a molecular oxygen-containing gas and an inert diluent at a total pressure in the range of 1 to 100 bar and wherein the partial pressure of the molecular oxygen-containing gas is such that the temperature of the catalyst is maintained within the range of 225 to 325°C.

2. A process according to claim 1 in which the catalyst is regenerated in a first regeneration and in at least one subsequent regeneration.

3. A process according to claim 2 wherein the catalyst is regenerated in a first regeneration and up to four subsequent regenerations.

4. A process according to claim 2 wherein at least one subsequent regeneration is carried out at a different catalyst temperature and/or a different molecular oxygen-containing gas partial pressure to the first regeneration and such that the catalyst temperature is maintained within the range 225 to 325°C.

5. A process according to claim 1 wherein during the course of a regeneration at least one of the catalyst temperature and the partial pressure of the molecular oxygen-containing gas is adjusted and such that the catalyst temperature is maintained within the range of 225 to 325°C.

6. A process according to claim 1 wherein the molecular oxygen-containing gas is selected from molecular oxygen and air.

7. A process according to claim 1 wherein the molecular oxygen-containing gas is present in the regenerating gas at a concentration in the range of 0.1 to 25 mol % based on the total of the concentration of the molecular oxygen-containing gas and the concentration of the inert diluent.

8. A process according to claim 1 wherein the inert diluent is selected from nitrogen, helium, argon, carbon dioxide and mixtures thereof.

9. A process according to claim 1 wherein the regeneration is carried out at a total pressure in the range of 1 to 80 bar.

10. A process according to claim 1 wherein the partial pressure of the molecular oxygen containing gas is in the range of 0.05 to 2 bar.

11. A process according to claim 1 wherein the regenerating gas has a gas hourly space velocity in the range of 500 to 10,000 h'.

12. A process according to claim 1 wherein the catalyst is contacted with the regenerating gas for a period of time in the range of 1 to 100 hours.

13. A process according to claim 1 wherein the catalyst is mordenite in the acid (Hform) or is loaded with one or more metals selected from copper, silver, gold, nickel, iridium, rhodium, platinum, palladium and cobalt.

14. A process according to claim 1 wherein the catalyst is regenerated in-situ using the following steps:
   (i) ceasing contact of the catalyst with the carbonylatable reactant, carbon monoxide and hydrogen;
   (ii) purging the reactor with an inert gas;
   (iii) regenerating the catalyst with the regenerating gas to remove hydrocarbon deposits from the catalyst;
   (iv) terminating the regeneration; and
   (v) resuming contact of the catalyst with the carbonylatable reactant, carbon monoxide and hydrogen.

15. A process according to claim 14 wherein prior to step (v) the reactor is purged with an inert gas.

* * * * *